United States Patent
Spahn et al.

(10) Patent No.: US 10,350,102 B2
(45) Date of Patent: *Jul. 16, 2019

(54) INFLATABLE FOOT CUSHION

(71) Applicant: EHOB, Inc., Indianapolis, IN (US)

(72) Inventors: James G. Spahn, Carmel, IN (US);
Brian D. Conway, Carmel, IN (US);
David P. Laughlin, Mooresville, IN (US); Scott D. Rogers, Carmel, IN (US)

(73) Assignee: EHOB, Inc., Indianapolis, IN (US)

(*) Notice: Subject to any disclaimer, the term of this patent is extended or adjusted under 35 U.S.C. 154(b) by 306 days.

This patent is subject to a terminal disclaimer.

(21) Appl. No.: 15/294,213

(22) Filed: Oct. 14, 2016

(65) Prior Publication Data

US 2017/0027733 A1 Feb. 2, 2017

Related U.S. Application Data

(63) Continuation of application No. 14/146,798, filed on Jan. 3, 2014, now Pat. No. 9,517,154, and a continuation-in-part of application No. 13/432,068, filed on Mar. 28, 2012, now Pat. No. 9,301,866.

(60) Provisional application No. 61/748,561, filed on Jan. 3, 2013, provisional application No. 61/516,087, filed on Mar. 29, 2011.

(51) Int. Cl.
*A61F 5/01* (2006.01)
*A61F 5/058* (2006.01)
*A61F 13/06* (2006.01)

(52) U.S. Cl.
CPC ............ *A61F 5/012* (2013.01); *A61F 5/0111* (2013.01); *A61F 5/0127* (2013.01); *A61F 5/05816* (2013.01); *A61F 13/069* (2013.01); *A61F 2005/0183* (2013.01); *A61H 2201/1697* (2013.01)

(58) Field of Classification Search
CPC ...... A61F 5/012; A61F 5/05816; A61F 13/04; A61M 13/00; A61B 17/1325; A61B 17/1355; A61B 17/1327; A61B 17/1322; A61B 17/132; A61B 5/02233; A61H 2201/5074; A61H 2205/027; A61H 2205/067

See application file for complete search history.

(56) References Cited

U.S. PATENT DOCUMENTS

| | | | |
|---|---|---|---|
| 4,266,298 A | 5/1981 | Graziano | |
| 4,722,332 A * | 2/1988 | Saggers | A61H 9/0078 128/DIG. 20 |
| 5,328,445 A | 7/1994 | Spahn et al. | |
| 9,517,154 B2 * | 12/2016 | Spahn | A61F 5/0195 |
| 2003/0191420 A1 | 10/2003 | Kuper et al. | |
| 2008/0294079 A1 | 11/2008 | Sterling et al. | |

* cited by examiner

*Primary Examiner* — Ophelia A Hawthorne
(74) *Attorney, Agent, or Firm* — Carson LLP; Michael D. Smith (57) ABSTRACT

An inflatable foot cushion including: an anterior side; a posterior side; an inflatable main chamber adapted to support with static air pressures the calf, ankle and foot of a body in a supine position, and an inflatable independent chamber.

4 Claims, 9 Drawing Sheets

INFLATABLE FOOT CUSHION

CROSS REFERENCE TO RELATED APPLICATIONS

The present application is a continuation of U.S. patent application Ser. No. 14/146,798 entitled "Inflatable Foot Cushion", filed Jan. 3, 2014, now U.S. Pat. No. 9,517,154, and claims priority to U.S. Provisional Patent Application Ser. No. 61/748,561 entitled "Inflatable Foot Cushion", filed Jan. 3, 2013, and is a Continuation-In-Part of U.S. patent application Ser. No. 13/432,068 entitled "Inflatable Foot Cushion", filed Mar. 28, 2012, now U.S. Pat. No. 9,301,866, which claims priority to U.S. Provisional Patent Application Ser. No. 61/516,087 entitled "Inflatable Foot Cushion", filed Mar. 29, 2011.

BACKGROUND

The present invention relates generally to the field of inflatable devices for supporting the human body, and more particularly is concerned with a novel improved inflatable foot cushion to counter the force amplifications experienced by the foot, and particularly the heel area of the foot, when the body is in, the supine position.

In the supine position, the foot assumes the shape of a wedge that tapers from the toes down to the heel. The mechanical force amplifications that are typically associated with a wedge are therefore also experienced by the wedge-shaped foot. The heel area, and more specifically the points of contact between the heel area and the patient support surface or substrate upon which the body is lying in the supine position, experiences mechanical force amplifications that are analogous to those experienced by the working edge of the typical wedge. In addition, when in the supine position, the lower legs function as levers with the heel areas serving as fulcrums, further amplifying the mechanical forces acting upon the heel areas.

The recognition that heel ulcers are caused by such mechanical forces (pressure, shear and frictional stresses) on the heel became clinically significant in the early 1980's. Since that time it has been found that offloading mechanical forces on the heel is the ideal way to prevent a pressure ulcer of the heel from developing (see NPUAP and EPUAP Guidelines). During the era of using pillows to offload mechanical forces on the heel, the occurrence of pressure ulcers of the heel continued to increase. Pressure ulcers of the heel are now running a close second to sacral pressure ulcers. When considering the deep tissue injury component of the pressure ulcer, pressure ulcers of the heel are now first in occurrence (see Vangilder, MacFarlane, Harrison, Lachenbruch and Meyer 254-261).

In 1994, a three-chambered inflatable foot cushion was patented (Inflatable Foot Cushion of U.S. Pat. No. 5,328,445). The prevention and treatment of pressure ulcers of the heel and other types of foot wounds have been exceptional when this patented inflatable foot cushion has been in use. The foot resting chamber of that device was constructed to resemble the keel of a boat. The objectives of the two main inflatable chambers of the patented inflatable foot cushion that defined the foot resting chamber were the offloading the mechanical forces on the heel; the giving of symmetrical static air support to the calf, ankle and foot; and (3) the supporting of the sole of the foot to prevent foot drop and resultant injury. The third main chamber of that patented inflatable foot cushion was an independent chamber (16) that was used beneath the two main chambers as an accessory chamber to elevate the inflatable foot cushion.

In 2011, an improved inflatable foot cushion over the Inflatable Foot Cushion of U.S. Pat. No. 5,328,445 was disclosed in U.S. Pat. No. 9,301,866.

SUMMARY

The present invention provides further improvements to the inflatable foot cushion of U.S. Pat. No. 9,301,866, and to the Inflatable Foot Cushion of U.S. Pat. No. 5,328,445, the disclosures of which are both incorporated herein by reference in their entireties. The novel improvements of the present invention relate to the independent inflatable chamber 10 of U.S. Pat. No. 9,301,866, and to the inflatable cushion (16) of U.S. Pat. No. 5,328,445, which improvements provide better protection of the Achilles' tendon areas of patients who wear the improved inflatable foot cushion 21 of the present invention (see FIG. 9); provide for better unloading of pressures on the heels of patients; that provide for reduced left and right lateral rotations of the ankles of patients; and that provide for less stress on the materials of construction upon rotation of the improved inflatable chamber 22a under the improved inflatable foot cushion 21 of the present invention.

One embodiment of the improved inflatable foot cushion of the present invention to reduce the force amplifications upon the heel of a foot received therein when the body is in a supine position is the improvement comprising means for increasing the volume of the inflatable chamber of the inflatable foot cushion that pivotally swings under the inflatable foot cushion to provide increased support for the inflatable foot cushion when it is placed upon a patient support surface or substrate.

Another embodiment of the improved inflatable foot cushion of the present invention to reduce the force amplifications upon the heel of a foot received therein when the body is in a supine position is the further improvement comprising means to improve the pivotal axis about which the larger volume inflatable chamber is pivotally swung under the inflatable foot cushion of the present invention to reduce the bunching of the construction material.

Another embodiment of the improved inflatable foot cushion of the present invention to reduce the force amplifications upon the heel of a foot received therein when the body is in a supine position is the further improvement comprising, means to increase the volume of the main chamber of the inflatable foot cushion in the direction of the larger volume inflatable chamber whereby two lateral bladders are created on either side of the main chamber volume expansion and between which the larger volume inflatable chamber is cradled when the larger volume inflatable chamber is pivoted under the inflatable foot cushion which thereby provides improved lateral stability to the inflatable foot cushion.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

Corresponding reference characters indicate corresponding parts throughout the several views. The exemplary embodiments set forth herein are not to be construed as limiting the scope of the invention in any manner.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Figure 1:
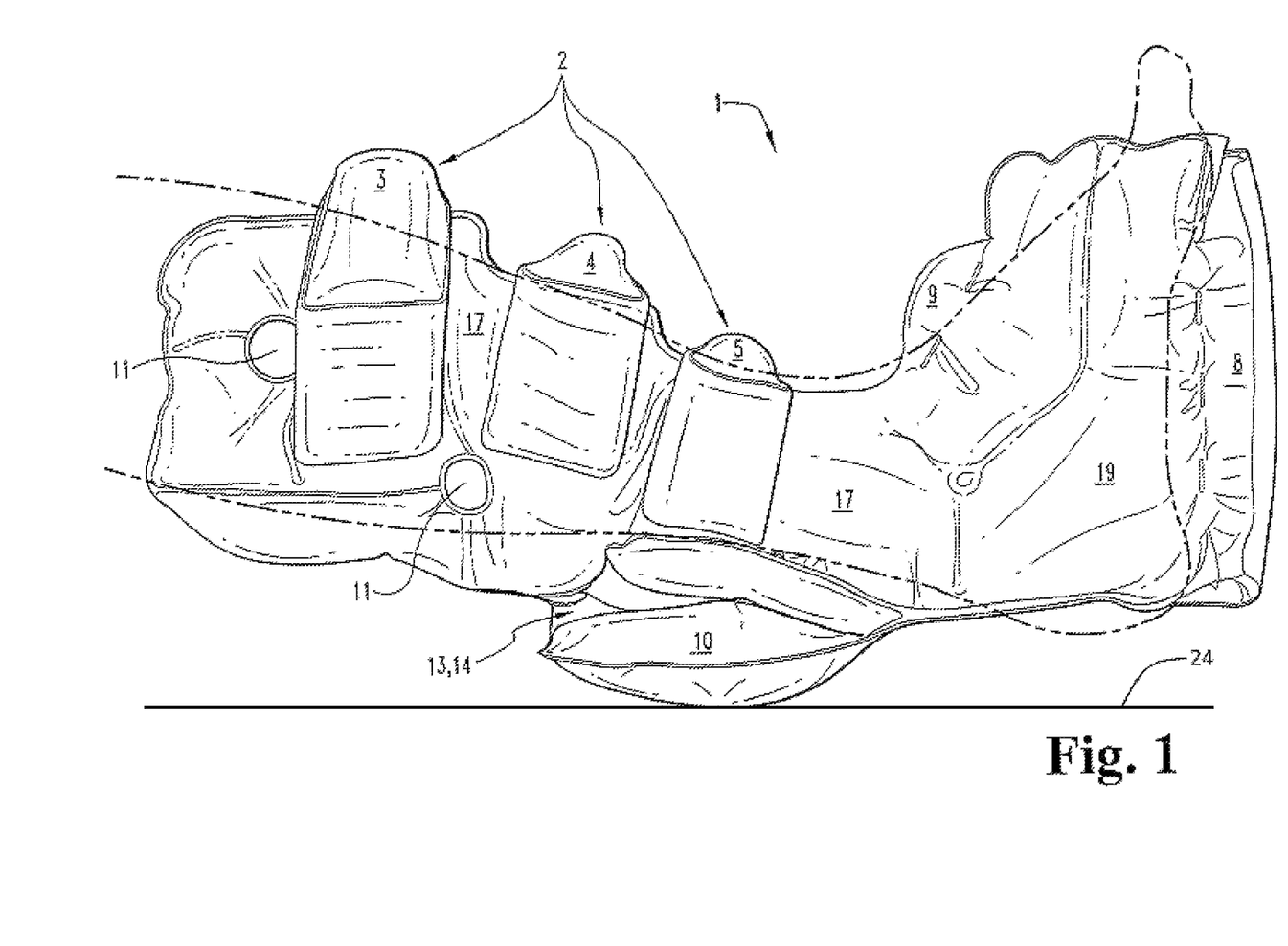
FIG. 1 is a right side elevation view of the novel inflatable foot cushion of U.S. Pat. No. 9,301,866.

Thus, all of the implementations described below are exemplary implementations provided to enable persons skilled in the art to make or use the embodiments of the disclosure and are not intended to limit the scope of the disclosure, which is defined by the claims. As used herein, the word "exemplary," or "illustrative" means "serving as an example, instance, or illustration." Any implementation described herein as "exemplary" or "illustrative" is not necessarily to be construed as preferred, or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 8:
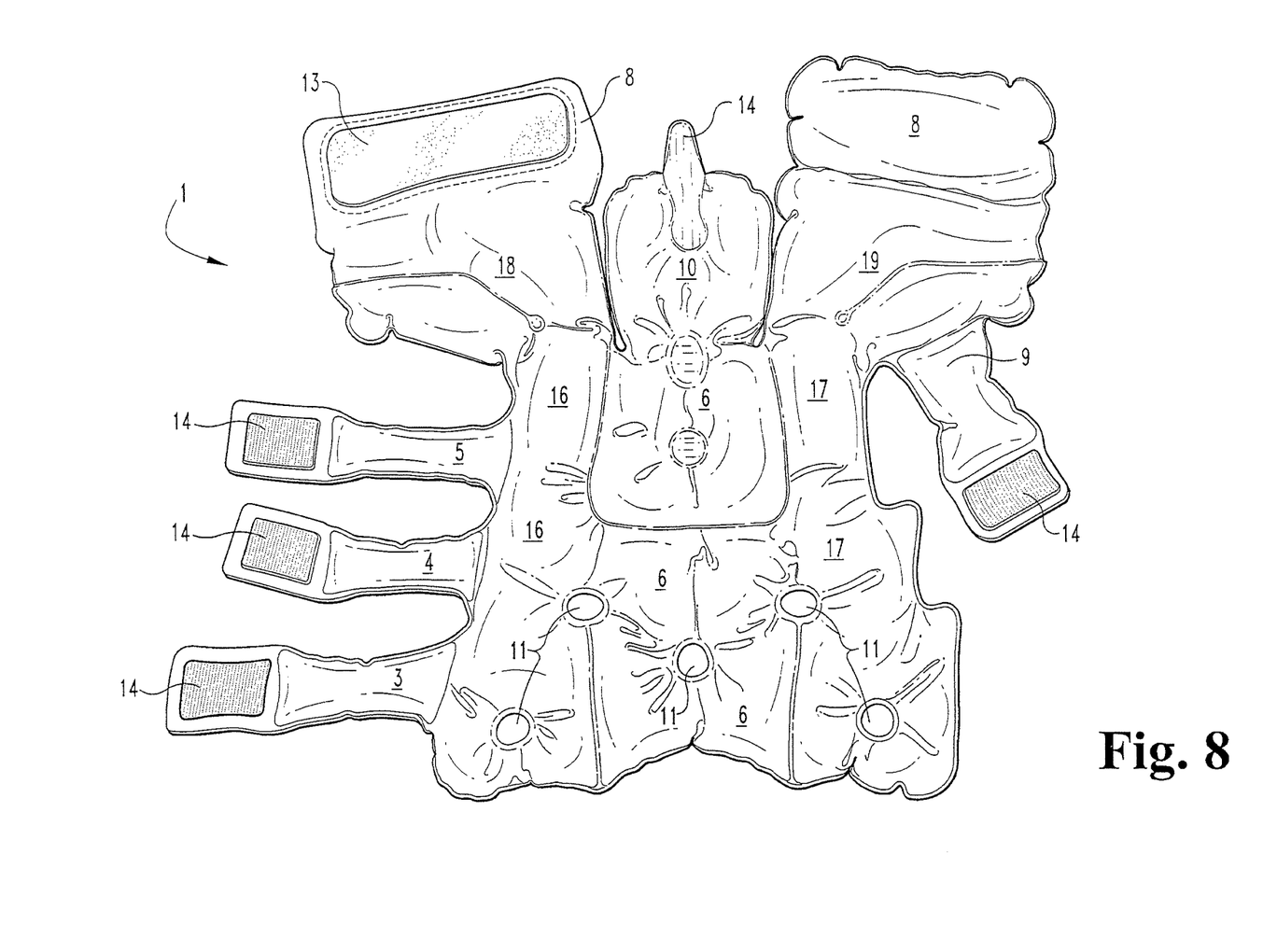
FIG. 8 is an exploded top plan view of the inflated inflatable foot cushion of FIG. 1 rotated 180 degrees, showing the relationships of its constituent parts.

Referring now to FIG. 8, which is an exploded top plan view of the inflatable foot cushion 1 of U.S. Pat. No. 9,301,866, FIG. 8 illustrates the relationships of the novel constituent parts of that inflatable foot cushion, and which also illustrates how two pliable plastic sheets have been joined together by conventional means to form the novel inflatable chambers and straps of the inflatable foot cushion 1 of U.S. Pat. No. 9,301,866.

Figure 2:
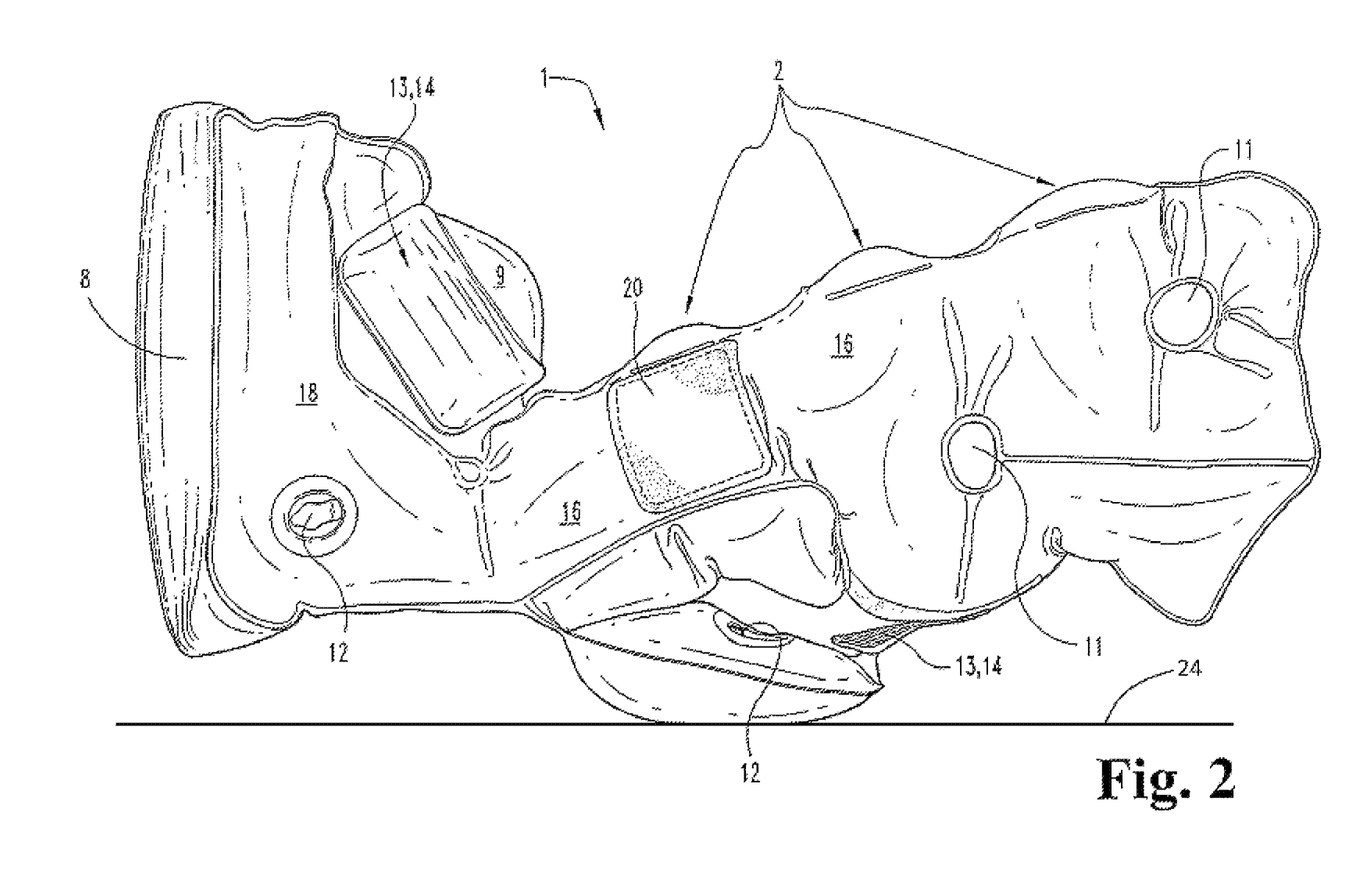
FIG. 2 is a left side elevation view of the inflatable foot cushion of FIG. 1.

Referring to FIG. 2, there is one inflation port 12 for all of the air-inflatable chambers shown in FIG. 8, all of which are in fluid communication with each other, with one exception. FIG. 2 also illustrates an inflation port 12 for independent air-inflatable chamber 10, which is not in fluid communication with the other chambers illustrated in FIG. 8, and which is of the same size and has the same functionality as does independent air-inflatable cushion (16) of the Inflatable Foot Cushion (10) of U.S. Pat. No. 5,328,445. The only difference between the independent inflatable chamber 10 of U.S. Pat. No. 9,301,866, and the inflatable cushion (16) of U.S. Pat. No. 5,328,445 is that cushion 10 is kept in its adjustable positions by hook and loop fasteners 13, 14.

One of the improvement of the inflatable foot cushion 1 of U.S. Pat. No. 9,301,866 is the addition of air-inflated, adjustable calf straps 2 that secure the inflatable foot cushion 1 to the calf, ankle and foot of a patient, which air-inflated calf straps 2 effectively protect a patient's skin of the calf over the tibia when the calf is secured within the inflatable foot cushion 1 by the inflated adjustable calf straps 2. This is accomplished by filling the individual inflatable calf straps 3, 4, 5 with static air, each strap being formed, as are all other static air chambers of the inflatable foot cushion 1, by two pliable plastic sheets joined together by conventional means to form inflatable chambers within the calf straps 3, 4, 5. Filling the calf straps 3, 4, 5 with air moves the welded joints 7 of the two pliable plastic sheets that were joined together to form the air chambers within the calf straps 3, 4, 5 well away from a patient's skin of the calf over the tibia when the calf straps 3, 4, 5 are each independently snugged up against the skin of the calf over the tibia to secure the improved inflatable foot cushion 1 of U.S. Pat. No. 9,301,866 about the calf, ankle and foot of the patient. The inflatable calf straps 3, 4, 5 are each connected at one end thereof to one downwardly-sloping side 16 of the main chamber 6, and in fluid communication with the main chamber 6. The other end of each calf strap 3, 4, 5 is adjustably attached to the opposite downwardly sloping side 17 of the main chamber 6 with hook and loop fasteners 13, 14.

By this design of the secured inflated calf straps 3, 4, 5 of the inflatable foot cushion 1 of U.S. Pat. No. 9,301,866, the calf and ankle are fully supported and kept snug through 360 degrees by equalized static air pressures (Cf. Boyle's Law and Pascal Principle). Not only do the air-filled calf straps 3, 4, 5 deliver non-gradient air pressure to the calf, but as mentioned above, they also keep the sealed construction edges 7 of the air-filled straps 3, 4, 5 away from the patient's skin of the calf over the tibia. Neither of these design features was present in the Inflatable Foot Cushion (10) of U.S. Pat. No. 5,328,445.

Another improvement of the inflatable foot cushion 1 of U.S. Pat. No. 9,301,866 is the sloped-downward design of the sides 16, 17 of the main chamber 6, which slope downwardly from the calf to the ankle areas of the main chamber 6 (see FIG. 1). The use of the air filled calf straps 3, 4, 5 allows this lower side profile of the sides 16, 17 of the main chamber 6 to be used effectively to provide for better ambient air circulation around the calf and ankle area, which in combination with through holes 11 in the sides 16, 17 provides for better ambient air control (both temperature and moisture control) around the patient's calf and ankle. The inflatable foot cushion 1 of U.S. Pat. No. 9,301,866 thus permits more ambient air to enter the interior of inflatable foot cushion 1 and surround the patient's calf and ankle areas. To improve ambient air circulation, calf strap 5 may be freed from its securing hook and loop fasteners 13, 14 on side 17 of the main chamber 6, and the hook fastener 14 of calf strap 5 may be temporarily attached to loop fastener 20 located on side 17 of main chamber 6 (see FIG. 2).

In testing done to date, the lower side profile of the downwardly-sloping sides 16, 17 of the main chamber 6 of U.S. Pat. No. 9,301,866 also reduced the chance for lateral rotation of the patient's calf, ankle and foot within the main chamber 6, and reduces the chances for an over extension or flexion of the patient's knee and a lateral rotation of the patient's hip. This was a major improvement over the Inflatable Foot Cushion of U.S. Pat. No. 5,328,445, as that device is balloon-like in its overall structure, and it therefore had a tendency to roll from side-to-side when either over-inflated or underinflated with air. The lower profile and downwardly sloping sides 16, 17 also allow patients wearing the inflatable foot cushion 1 of U.S. Pat. No. 9,301,866 to articulate their ankles and to move their foot fore and aft while it is snuggly embraced within the inflatable foot cushion 1 of U.S. Pat. No. 9,301,866.

Additional improvements of the inflatable foot cushion 1 of U.S. Pat. No. 9,301,866, discussed below, relate to preventing the inflatable foot cushion 1 from spinning on its longitudinal axis, which compromises the desired patient calf, ankle and foot positioning within the inflatable foot cushion, and which occurred at times when the Inflatable Foot Cushion (10) of U.S. Pat. No. 5,328,445 was in use.

Another improvement of the inflatable foot cushion 1 of U.S. Pat. No. 9,301,866 is a novel air-filled and adjustable foot strap 9 that is connected to and in fluid communication with the foot chamber cushion 19 of the main chamber 6. Adjustable foot strap 9 is extendible from foot chamber cushion 19 to foot chamber cushion 18, where it is adjustably attached to foot cushion chamber 18 of the main chamber 6 with hook and loop fasteners 13, 14. In this manner, the air-filled and adjustable foot strap 9 covers the patient's skin on top of the foot surrounded by the main chamber 6, which prevents the patient's calf, ankle and foot from inadvertently slipping out of the inflatable foot cushion 1 when in use. The foot strap 9 also allows for a complete customizable fitting of a patient's foot within the inflatable foot cushion 1. This novel feature can be compared to the lacing or strapping of normal footwear to the patient's foot.

Figure 6:
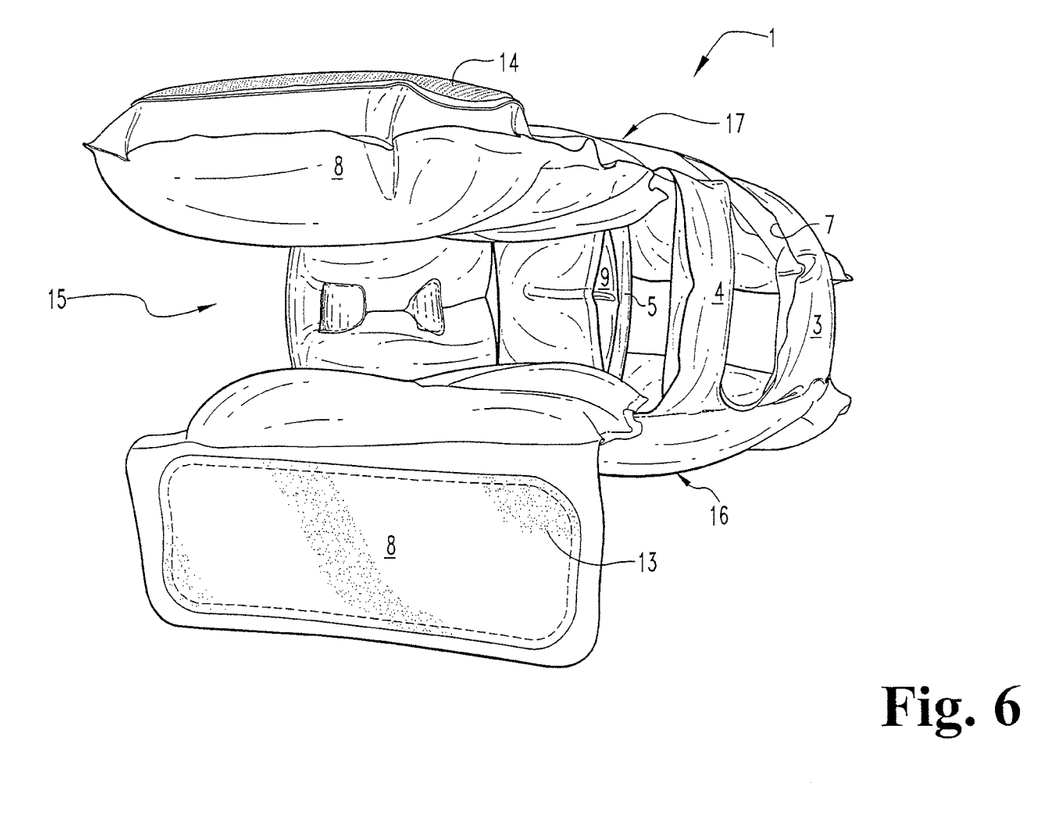
FIG. 6 is a front perspective view of the inflatable foot cushion of FIG. 1, rotated 90 degrees.
Figure 7:
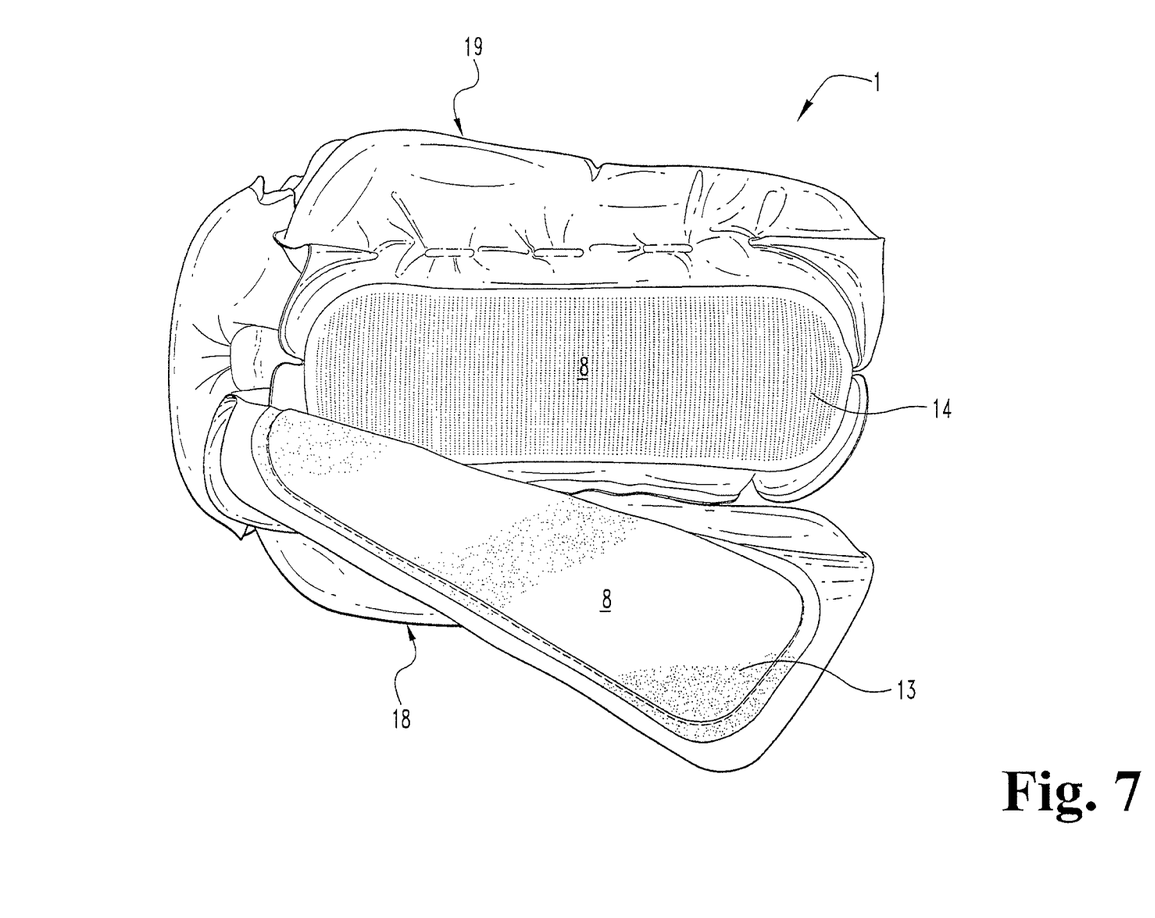
FIG. 7 is a front end view of the inflatable foot cushion of FIG. 1, rotated 90 degrees.

Another improvement of the inflatable foot cushion 1 of U.S. Pat. No. 9,301,866 is the novel design of the adjustable, inflatable foot sole cushion 8 that is adjustable in two parts (see FIGS. 6 and 7) with hook and loop fasteners 13, 14 to match the contours of the sole of a foot within the inflatable foot cushion 1. As best shown in FIG. 8, the adjustable and inflatable two-part foot sole cushion 8 has its first part thereof in fluid communication with foot chamber cushion 18, and its second part in fluid communication with foot chamber cushion 19 and the first part of the foot sole cushion 8, thereby allowing a more custom fit of the inflatable foot cushion 1 to the sole of a patient's foot. It is adjustable with large hook and loop fasteners 13, 14 (see FIGS. 6 and 7), which also protects the sides of a patient's foot from being too tightly fitted within inflatable foot cushion 1. The uniform shape of the foot sole cushion (14) of the Inflatable Foot Cushion (10) of U.S. Pat. No. 5,328,445 was not able to accomplish this custom fit to the sole of a patient's foot.

Figure 3:
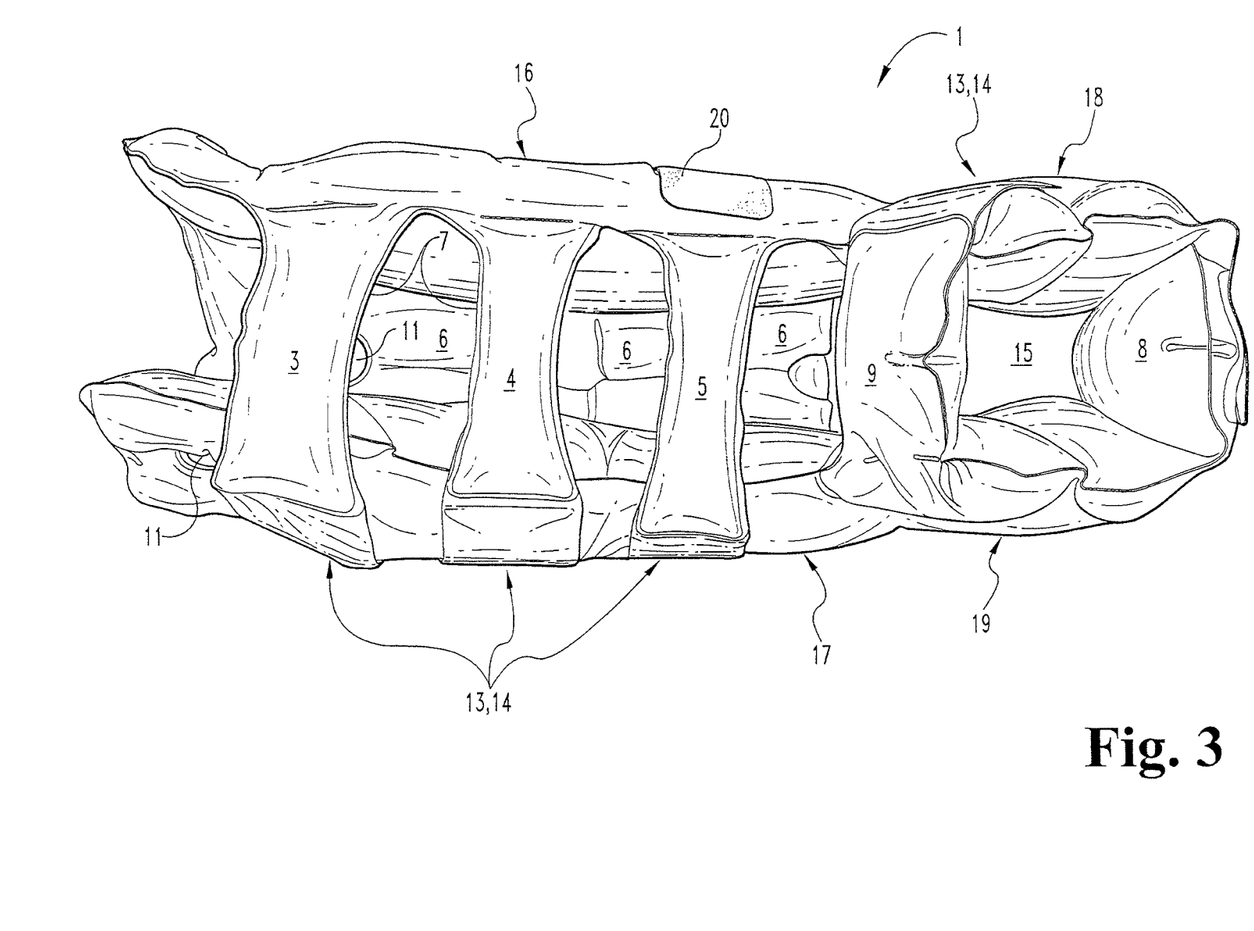
FIG. 3 is a top plan view of the inflatable foot cushion of FIG. 1.
Figure 4:
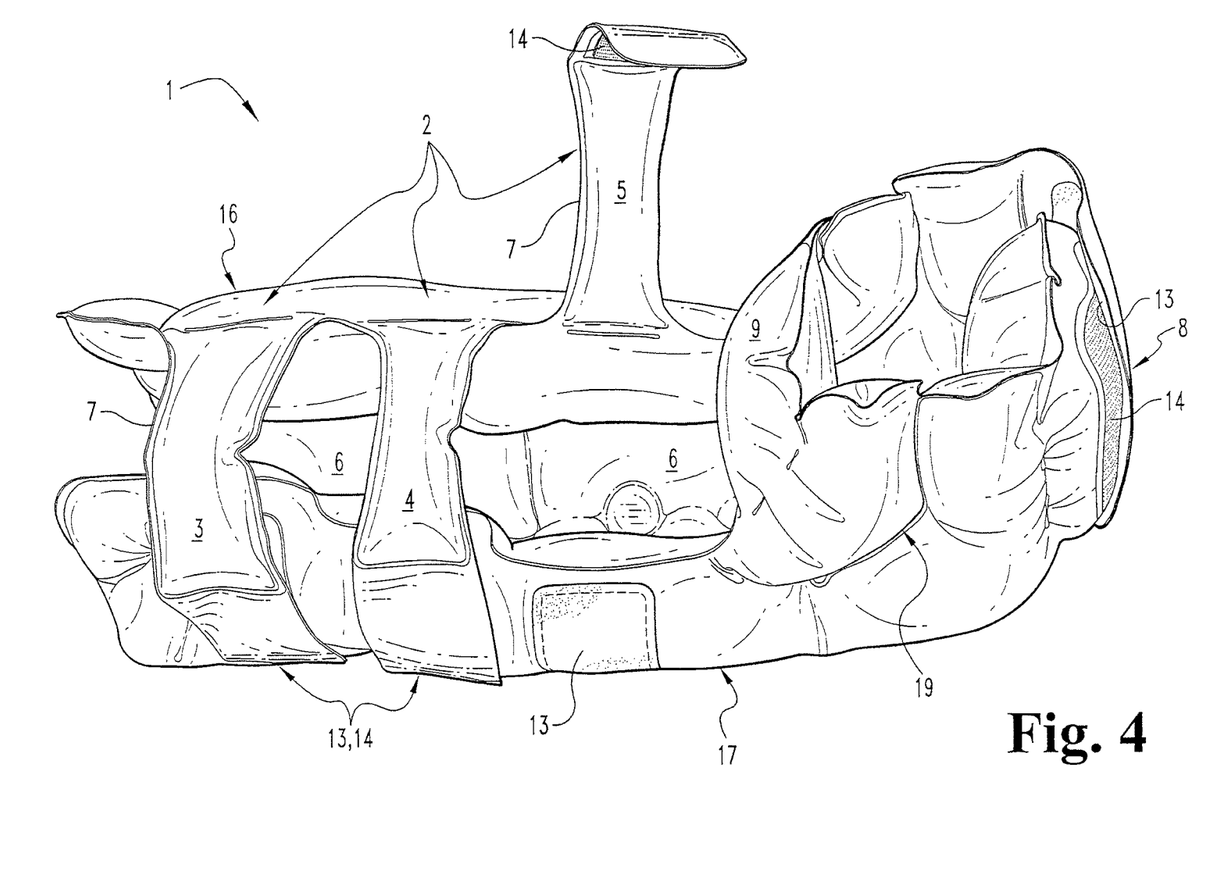
FIG. 4 as a right side perspective view of the inflatable foot cushion of FIG. 1.
Figure 5:
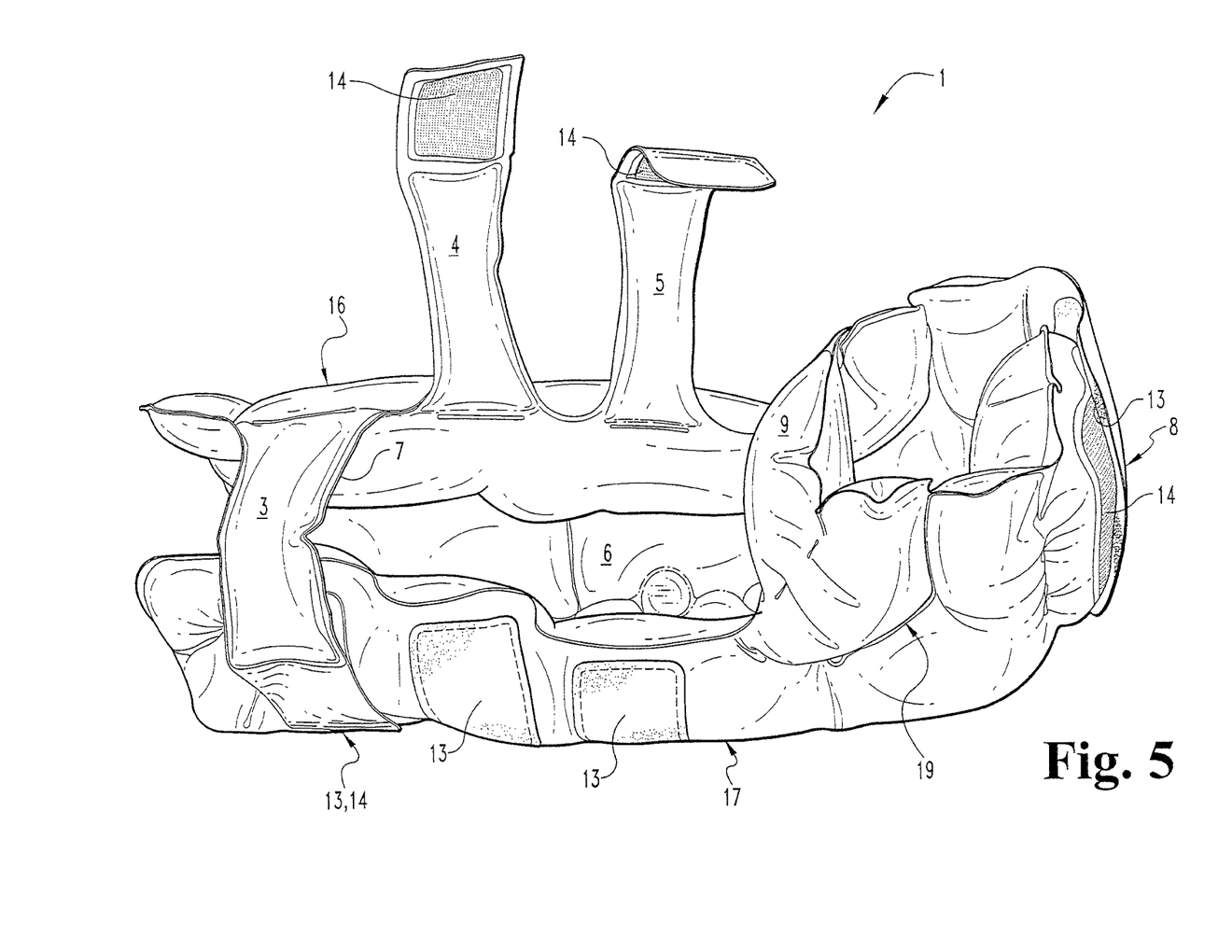
FIG. 5 is a right side perspective view of the inflatable foot cushion of FIG. 1.

The adjustable inflatable two-part foot sole cushion 8 also creates a desirably larger hole 15 in inflatable foot cushion 1 for a patient's heel to reside within, unsupported (see FIGS. 1, 3 and 6), relative to the hole ("through space" 84) in the Inflatable Foot Cushion (10) of U.S. Pat. No. 5,328,445. This, coupled with the functionality of foot strap 9 and foot sole cushion 8 which keep a patient's foot up, thereby preventing "foot drop" (see FIG. 1), was also thought to protect the entire Achilles' heel area, as well.

Furthermore, when the two-part foot sole cushion 8 is opened completely by disassociating the adjustable hook and loop fasteners 13, 14 completely (see FIG. 7), the patient's foot sole is fully exposed, and the patient could then become ambulatory, moving from a bed to a chair, for example, while still wearing the inflatable foot cushion 1 of U.S. Pat. No. 9,301,866, which was not a possibility with the Inflatable Foot Cushion (10) of U.S. Pat. No. 5,328,445.

In testing to date, the above-mentioned third and fourth improvements disclosed in U.S. Pat. No. 9,301,866 also assisted in preventing the spinning of the inflatable foot cushion 1 of U.S. Pat. No. 9,301,866 on its longitudinal axis, which occurred at times when the Inflatable Foot Cushion 10 of U.S. Pat. No. 5,328,445 was overinflated or underinflated. These improvements of the inflatable foot cushion 1 of U.S. Pat. No. 9,301,866 maintain proper anatomical positioning of the patient's calf, ankle and foot when in that inflatable foot cushion, and provide a low-profile static air support through 360 degrees for the patient's calf, ankle and foot so that skin and soft tissue distortion, ischemia, lymphatic and interstitial fluid obstruction and reperfusion injuries were less likely to occur.

The following two tables summarize in tabular format the differences between the inflatable foot cushion 1 of U.S. Pat. No. 9,301,866 ("2011 Device") and the Inflatable Foot Cushion (10) of U.S. Pat. No. 5,328,445 ("1994 Device").

TABLE I

|  | 1994 Device | 2011 Device |
| --- | --- | --- |
| Delivers Static Air Support to the Calf/Ankle/Foot ("CAF") | Yes | Yes |
| Offloads the Heel | Yes | Yes |
| Protects Achilles' Tendon | Yes | Yes |
| Has Air Filled, Adjustable Strapping | No | Yes |
| Protects the Medial Malleolus | Yes | Yes |

TABLE II

| Rating of Effectiveness 1-5 | | |
| --- | --- | --- |
|  | 1994 Device | 2011 Device |
| Unloads the Heel | 5 | 5 |
| Delivers Non-Gradient Static Air Support | 5 | 5 |
| Addresses Microclimate (Heat, Moisture) | 4 | 5 |
| Prevents Foot Drop | 3 | 4 |
| Prevents Lateral Rotation | 3 | 4 |
| Prevents Over-Extension of the Knee | 4 | 5 |
| Safety of the Adjustable Straps | 4 | 5 |
| Foot Compartment Customizing Ability | 2 | 5 |
| Prevention of the CAF Spinning, and Improper Positioning | 3 | 5 |
| Ease of Use | 4 | 5 |
| Cost Effective | 5 | 5 |

(5 = Excellent-1 = Poor)

Figure 9:
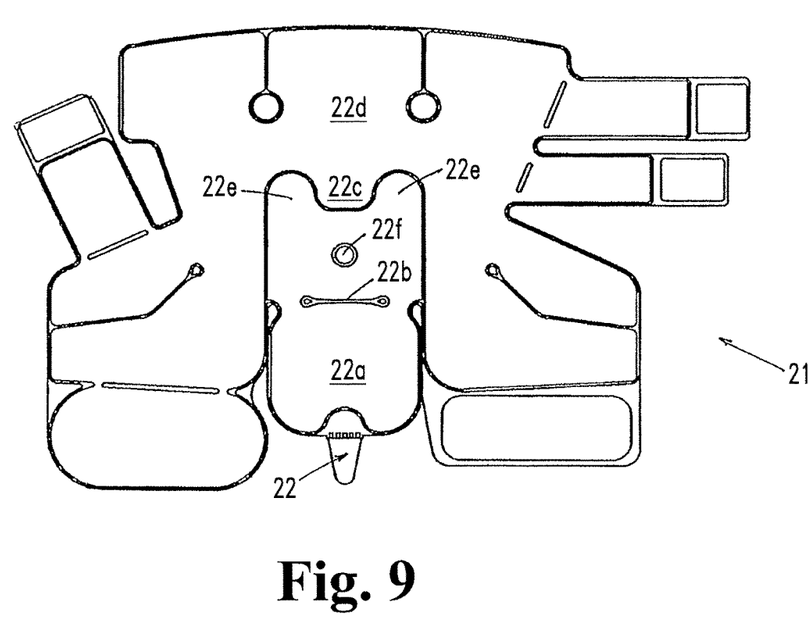
FIG. 9 is an exploded top plan view of the novel inflated inflatable foot cushion of the present invention showing the relationships of its consistent parts.

Referring now to the inflatable foot cushion 21 of FIG. 9, the novel improvements of the present invention that have been made to the inflatable foot cushion 1 of U.S. Pat. No. 9,301,866, and to the Inflatable Foot Cushion (10) of U.S.

Pat. No. 5,328,445, include a novel improvement to the hook and loop fastener 22, which is performing essentially the same function as it does on inflatable chamber 10 of U.S. Pat. No. 9,301,866, and on inflatable cushion (16) of U.S. Pat. No. 5,328,445, but which is now decreased in its overall length in the present invention. This decrease in length of hook and loop fastener 22 of the present invention creates a larger inflatable chamber 22a of the present invention, which increases the inflated volume size of chamber 22a when it is pivoted under the novel inflatable foot cushion 21 of the present invention. This provides increased support for the patient's foot over any patient support surface or substrate 24 (FIGS. 1 and 2) on which the novel inflatable foot cushion 21 of the present invention is placed.

The next novel improvement of the inflatable foot cushion 21 of the present invention is the novel lateral seal 22b that replaces the oval-shaped pivot point of inflatable chamber 10 of U.S. Pat. No. 9,301,866, and the inflatable cushion (16) of U.S. Pat. No. 5,328,445. The novel lateral seal 22b creates a much-improved pivotal axis for the larger inflatable cushion 22a of the present invention when it is pivoted underneath the novel inflatable foot cushion 21 of the present invention. The novel lateral seal 22b also reduces the bunching of the material of construction that was present when inflatable chamber 10 of U.S. Pat. No. 9,301,866, and inflatable cushion (16) of U.S. Pat. No. 5,328,445, were pivoted about their oval-shaped pivot points, which resulted in bunched material of construction that proved to be potentially damaging to the Achilles' tendon areas of patients who wore these inflatable foot cushions. The novel lateral seal 22b of the present invention also gives better elevation to the heel of a patient who is wearing of the inflatable foot cushion 21 of the present invention because the novel lateral seal 22b keeps the larger inflatable cushion 22a at a greater height off of any patient support surface or substrate 24 when it is pivoted about novel lateral seal 22b under the novel inflatable foot cushion 21 of the present invention. This also puts less physical strain on the material of construction of the novel inflatable foot cushion 21.

The next novel improvement of the novel inflatable foot cushion 21 of the present invention is the extension 22c of its main chamber 22d. This increases in the volume of main chamber 22d providing more elevation of the main chamber 22d over any patient support surface or substrate 24 at the center of the novel inflatable foot cushion 21, and most importantly, it creates two lateral bladders 22e between which inflatable cushion 22a is cradled when the inflatable cushion 22a is pivoted under the novel inflatable foot cushion 21 of the present invention. The two lateral bladders 22e provide much improved lateral stability to the novel inflatable foot cushion 21 of the present invention since the two lateral bladders 22e are at about the same height off of any patient support surface or substrate 24 as is the inflatable cushion 22a, which prevents the novel inflatable foot cushion 21 from rocking left to right on the round-bottomed inflatable cushion 22a when it is pivoted under the novel inflatable foot cushion 21 of the present invention.

The next novel improvement of the improved inflatable foot cushion 21 of the present invention is the smaller placation circle 22f. The smaller placation circle 22f increases the volume of the two lateral bladders 22e, and thus also increase the height of the novel inflatable foot cushion 21 off of any patient support surface or substrate 24 on which it is placed, which better protects a patient's lower calf and Achilles' tendon areas while wearing the novel inflatable foot cushion 21. The key is that the placation circle 22f is now smaller, which enlarges the volume of the two lateral bladders 22e.

In summary, the medical advantages provided by the novel improvements of the inflatable foot cushion 21 of the present invention over the inflatable foot cushions 1 of U.S. Pat. No. 9,301,866 and the Inflatable Foot Cushion (10) of U.S. Pat. No. 5,328,445, include: 1) better protection of the patient's Achilles' tendon areas; 2) better unloading of pressures on the patient's heels due to the increased elevation of the patient's heels off of patient support surfaces or substrates 24; and 3) left and right lateral rotation of the ankles of patients is avoided by two novel lateral cushions 22e formed by expanding the main chamber 22d of the improved inflatable foot cushion 21 of the present invention, which cradles and stabilizes the improved inflatable chamber 22a of the present invention when it is pivoted under the improved inflatable foot cushion 21.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in, the art to which this invention pertains and which fall within the limits of the appended claims.

The invention claimed is:

1. An inflatable foot cushion adapted to support the foot of a patient, said inflatable foot cushion comprising:
   an anterior side;
   a posterior side;
   an inflatable main chamber defining a main chamber volume and adapted to support with static air pressures the calf, ankle and foot of a body in a supine position, said inflatable main chamber comprising a first inlet port, said inflatable main chamber further comprising a first side and a second side wherein each of said first and second sides slopes downwardly from the calf area to the ankle area of the inflatable main chamber; and
   an inflatable independent chamber defining an independent chamber volume, the inflatable independent chamber not in fluid communication with the inflatable main chamber, said inflatable independent chamber comprising a second inlet port, said inflatable independent chamber further comprising a first end and a second end, said first end pivotally attached to said inflatable main chamber, said second end comprising a cooperative hook and loop fastener for adjustably, releasably attaching said second end to said posterior side of said foot cushion, wherein said main chamber volume is greater than said independent chamber volume.

2. The inflatable foot cushion of claim 1, wherein the independent chamber is pivotally connected to the foot cushion.

3. The inflatable foot cushion of claim 1, wherein said foot cushion is adapted for being disposed on a patient support surface while being worn by a patient, with the independent chamber disposed between the main chamber and the patient support surface.

4. The inflatable foot cushion of claim 3, wherein the independent chamber is inflated sufficiently to force a heel of a foot of a patient in a supine position wearing said foot cushion into a position completely displaced from the patient support surface.

\* \* \* \* \*